United States Patent [19]

Socci et al.

[11] Patent Number: 5,792,447

[45] Date of Patent: Aug. 11, 1998

[54] NAIL ENAMEL COMPOSITION

[75] Inventors: Robert L. Socci, Cedar Grove, N.J.; Anatoly Ismailer, Roslyn Heights, N.Y.

[73] Assignee: Kirker Enterprises, Inc., Paterson, N.J.

[21] Appl. No.: 749,469

[22] Filed: Nov. 15, 1996

[51] Int. Cl.$^6$ ............................................. A61K 7/04
[52] U.S. Cl. ................................... 424/61; 424/401
[58] Field of Search .................... 424/401, 61; 106/3

[56] References Cited

U.S. PATENT DOCUMENTS

| | | | |
|---|---|---|---|
| 3,466,223 | 9/1969 | Beeler et al. | 161/162 |
| 4,097,440 | 6/1978 | Maximovich et al. | 260/31.4 R |
| 4,301,046 | 11/1981 | Schlossman | 260/16 |
| 5,066,484 | 11/1991 | Castrogiovanni et al. | 424/61 |
| 5,145,670 | 9/1992 | Castrogiovanni et al. | 424/61 |
| 5,145,671 | 9/1992 | Castriogiovanni et al. | 424/61 |
| 5,180,847 | 1/1993 | Thurman et al. | 560/238 |
| 5,225,185 | 7/1993 | Castrogiovanni et al. | 424/61 |
| 5,227,155 | 7/1993 | Castrogiovanni et al. | 424/61 |

OTHER PUBLICATIONS

Kodaflex TXIB Product Brochure, undated.
Chemical Abstracts No. 1–164, various dates.

*Primary Examiner*—Thurman K. Page
*Assistant Examiner*—Sharon Howard
*Attorney, Agent, or Firm*—Lerner, David, Littenberg, Krumholz & Mentlik

[57] ABSTRACT

Nail enamel compositions include a primary film forming polymer, a solvent and one or more plasticizers, for example, compounds of

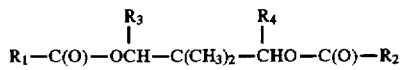

$$R_1-C(O)-OCH-C(CH_3)_2-CHO-C(O)-R_2$$

with $R_3$ and $R_4$ substituents on the indicated carbons wherein $R_1$ and $R_2$ are the same or different and represent linear or branched alkyl groups containing from one to 18 carbon atoms; and $R_3$ and $R_4$ are the same or different and represent linear or branched alkyl groups containing from one to five carbon atoms, provided that one of $R_3$ or $R_4$ may be hydrogen. The resulting nail enamel compositions are suitable for use as base coats, color coats, clear coats and protective top coats.

38 Claims, No Drawings

NAIL ENAMEL COMPOSITION

FIELD OF THE INVENTION

The present invention relates in general to nail enamel compositions, and more particularly, to such compositions which are suitable for use as base coats, color coats, clear coats and protective top coats for coating natural and synthetic nails. Still more particularly, the present invention relates to nail enamel compositions which include one or more plasticizers, for example, compounds of:

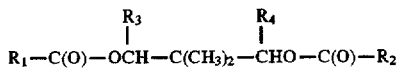

wherein $R_1$ and $R_2$ are the same or different and represent linear or branched alkyl groups containing from one to 18 carbon atoms, and $R_3$ and $R_4$ are the same or different and represent linear or branched alkyl groups containing from one to five carbon atoms, provided that one of $R_3$ or $R_4$ may be hydrogen.

BACKGROUND OF THE INVENTION

Nail enamel compositions include a class of nail care products regularly used by women as part of their beauty care routine. These nail care products are available in a multitude of product formulations, from clears to infinite colors. Typically, clear nail enamel compositions include a primary film forming polymer, a secondary film forming resin, a plasticizer and one or more solvents. In the case of a color nail enamel composition, the product will also include a thixotropic compound as a suspending agent and one or more pigments, or in the alternative, an organic coloring polymer may be used. In addition to these components, a number of optional and proprietary components are often included such as UV light absorbers, moisturizers, stabilizers, fragrances and the like.

Despite the diverse formulation differences between known nail enamel compositions, the desirable performance expectations are frequently the same, for example, smooth application, rapid dry time, scratch resistance, detergent and oil resistance, lustrous appearance and, often most importantly, wear and peel resistance. Accordingly, the present invention broadly discloses nail enamel compositions which include a novel class of plasticizers heretofore unknown for use in nail enamel compositions which possess the desirable performance expectations.

SUMMARY OF THE INVENTION

Broadly, in accordance with one embodiment of the present invention, there is disclosed nail enamel compositions which include one or more plasticizers selected from compounds of:

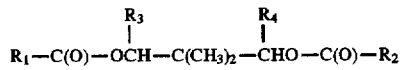

Wherein $R_1$ and $R_2$ are the same or different and represent linear or branched alkyl groups containing from one to 18 carbon atoms; and $R_3$ and $R_4$ are the same or different and represent linear or branched alkyl groups containing from one to five carbon atoms, provided that one of $R_3$ or $R_4$ may be hydrogen. The use of the aforementioned plasticizer enables the formulation of a variety of nail enamel compositions which are suitable for use as base coats, color coats, clear coats and protective top coats.

More specifically, the present invention discloses the novel use of 2,2,4-trimethyl-1,3-pentanediol diisobutyrate as a plasticizer in nail enamel compositions which evidence good wear and peel resistance, while at the same time, being safe to use with frequent applications.

In accordance with another embodiment of the present invention there is described a nail enamel composition comprising a film forming polymer, a solvent and a plasticizer comprising at least one or more compounds of the formula:

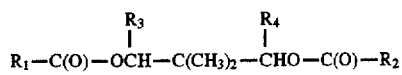

wherein $R_1$ and $R_2$ are the same or different and represent linear or branched alkyl groups containing from one to 18 carbon atoms; and $R_3$ and $R_4$ are the same or different and represent linear or branched alkyl groups containing from one to five carbon atoms, provided that one of $R_3$ or $R_4$ may be hydrogen.

In accordance with another embodiment of the present invention there is described a nail enamel composition comprising about 7 to 25% by weight of nitrocellulose, about 5 to 25% by weight of a film forming resin, about 55 to 80% by weight of at least one solvent, about 0.5 to 15% by weight of 2,2,4-trimethyl-1,3-pentanediol diisobutyrate, and optionally a thixotropic agent and at least one pigment.

With an endless list of possible compounds which are functionally suitable for use in a nail enamel composition, safety to the user in general, and to the fingernail in particular, is also a very important consideration. Heretofore, various techniques have been disclosed with respect to compositions of resins and solvents for improving, in particular, the safety factor against damage to the fingernail while, at the same time, maintaining the desirable properties of the nail enamel composition, e.g., good peel and wear resistance. In this regard, there is known a number of nail enamel components which are desirable of being removed from the formulation. For example, nail enamel compositions traditionally included a phthalate compound such as dibutyl phthalate as a plasticizer; an adhesion promoter or film forming resin such as a polymeric compound formed by condensation polymerization of formaldehyde or other aldehydes, typically an aromatic sulfonamide-aldehyde condensation resin such as o, p-toluene sulfonamide formaldehyde resin; and toluene as a diluent.

It is desirable that nail enamel compositions eliminate or reduced the amounts of phthalates, aldehydes (e.g., formaldehyde) condensation products and toluene in order to alleviate concerns that some wearers may be sensitized to the aforementioned components. In addition, the use of toluene in nail enamel compositions has been severely restricted in California under Proposition 65. However, attempts to formulate nail enamel compositions without the aforementioned components have uncovered difficulties because of the requirement to maintain the properties required of these compositions, such as long wear, high gloss, rapid dry time, resistance to chipping and peeling, and compatibility with other nail enamel components. In addition, these desired properties of nail enamel compositions are highly sensitive to changes in their components and to changes in the amounts of these components. Therefore, there is still the need for nail enamel compositions having improved wear and peel resistance and which exhibit satisfactory properties, as well as containing little or no undesirable components such as phthalates, aldehyde condensation products and/or toluene.

In accordance with another embodiment of the present invention there is described a toluene formaldehyde free nail enamel composition comprising a film forming polymer, a formaldehyde free film forming resin, one or more toluene free solvents and mixtures thereof, a plasticizer comprising at least one or more compounds of the formula:

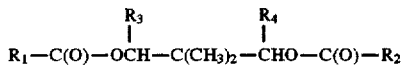

wherein $R_1$ and $R_2$ are the same or different and represent linear or branched alkyl groups containing from one to 18 carbon atoms; and $R_3$ and $R_4$ are the same or different and represent linear or branched alkyl groups containing from one to five carbon atoms, provided that one of $R_3$ or $R_4$ may be hydrogen, and optionally a thixotropic agent and at least one pigment.

In accordance with another embodiment of the present invention there is described a toluene formaldehyde free nail enamel composition consisting essentially of about 7 to 25% by weight of nitrocellulose, about 5 to 25% by weight of one or more formaldehyde free film forming resins and mixtures thereof, about 55 to 80% by weight of one or more toluene free solvents and mixtures thereof, about 0.5 to 15% by weight of a plasticizer consisting essentially of at least one or more compounds of the formula:

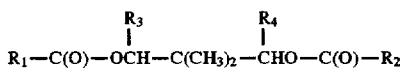

wherein $R_1$ and $R_2$ are the same or different and represent linear or branched alkyl groups containing from one to 18 carbon atoms; and $R_3$ and $R_4$ are the same or different and represent linear or branched alkyl groups containing from one to five carbon atoms, provided that one of $R_3$ or $R_4$ may be hydrogen, and optionally a thixotropic agent and at least one pigment.

These and other objects, features and advantages of the present invention, as well as details of the preferred embodiments thereof, will be more further understood from the following detailed description.

DETAILED DESCRIPTION OF THE PREFERRED EMBODIMENTS

Nail enamel compositions of the present invention for coating a natural or synthetic nail broadly include the ingredients of a primary film forming polymer, a plasticizer and a solvent. The resulting composition will provide a clear nail enamel, and may additionally include a secondary film forming resin. Where a colored nail enamel composition is desired, a thixotropic suspending agent and one or more pigments, or organic coloring polymers may be included in the composition. In addition to the above components, the nail enamel compositions according the present invention may further include one or more additional ingredients, for example, UV light absorbers, stabilizer, fragrances, moisturizers and the like. Nail enamel compositions of these components are useful in a wide variety of cosmetic applications such as base coats, color coats, clear coats and protective top coats.

The nail enamel compositions of the present invention contain one or more primary film forming polymers, for example, cellulose acetate, cellulose acetate butyrate, ethyl cellulose, vinyl polymers, nitrocellulose, as well as methacrylate and acrylate type polymers. The preferred primary film forming polymer for use in the present invention is nitrocellulose which provides an unusual combination of properties of toughness, durability, solubility and solvent release. Examples of nitrocellulose are the so called nitrocellulose RS ⅛ sec. and ½ sec.; nitrocellulose ½ sec.; and nitrocellulose RS 5–6 sec. and 60–80 sec., which have higher viscosities than the earlier grades. The term "RS" refers to the brand of nitrocellulose with a nitrogen content of about 11.2–12.8% with solubility in esters, ketones and glycol ethers manufactured by Hercules, Inc. The terms ⅛ sec., ¼ sec., ½ sec., 5–6 sec., etc. represent viscosity and refer to the time it takes for a ball to fall to a given depth in the material. Nitrocellulose is typically supplied in 70% concentrations, wet with 30% ethyl or isopropyl alcohol. As used in the present application, the percentage of nitrocellulose in a given composition will be on a dry basis.

The use of too small an amount of nitrocellulose tends to result in the coated films being easily damaged. On the other hand, the use of too large an amount of nitrocellulose can result in the coated film being too hard and inflexible, which easily causes undesirable peeling and hence poor wear resistance. Nail enamel compositions of the present invention include primary film forming polymers and combinations thereof in an amount ranging from about 7 to 25% by weight, and preferably in the range of about 10 to 15% by weight.

In addition to the primary film forming polymer, the nail enamel compositions of the present invention may also include an amount of one or more secondary film forming resins effective to strengthen the primary film forming polymer and to provide the nail enamel coating with acceptable gloss and adhesion characteristics. Exemplary secondary film forming resins which may be used in the present invention include, for example, drying and non-drying alkyd resins, polyvinyl resins for example polyvinyl acetate, polyester resins, acrylic polymers and copolymers, maleic modified glycerol esters of rosin and toluene sulfonamide/epoxy resins, e.g., tosylamide epoxy resin. It is also within the scope of nail enamel compositions of the present invention to include, if desired, aldehyde condensation products such as arylsulfonamide formaldehyde resins, specifically toluene sulfonamide formaldehyde resin which is a condensation product of formaldehyde and toluene sulfonamide. These secondary film forming resins are added to the nail enamel compositions of the present invention to strengthen and add acceptable wear characteristics to the primary film forming polymer. In general, the amount of secondary film forming resin ranges from about 5 to 25% by weight of the composition, and preferably about 8 to 15% by weight of the composition.

In addition to the primary film forming polymer and secondary film forming resin, the nail enamel compositions according to the present invention also include at least one plasticizer to soften and plasticize the primary film forming polymer. The preferred plasticizer which has heretofore been unknown for use in nail enamel compositions include compounds of:

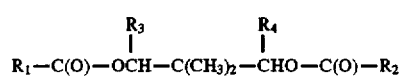

wherein $R_1$ and $R_2$ are the same or different and represent linear or branched alkyl groups containing from one to 18 carbon atoms, and $R_3$ and $R_4$ are the same or different and represent linear or branched alkyl groups containing from one to five carbon atoms, provided that one of $R_3$ or $R_4$ may be hydrogen. These plasticizers include compounds of 2,2, 4-trimethyl-1,3-pentanediol and derivatives thereof, such as its mono- and diisobutyrate esters, and most preferably 2,2,4-trimethyl-1,3-pentanediol diisobutyrate. Nail enamel compositions including the preferred plasticizer produced nail enamel coatings having excellent characteristics such as gloss and wear and peel resistance.

In combination with the preferred plasticizers, the nail enamel compositions of the present invention may also include one or more of the known plasticizers which are suitable for use in nail enamel compositions. Examples of such known plasticizers include tricresyl phosphate, dibutyl tartrate, benzyl benzoate, tributyl phosphate, butyl acetyl ricinoleate, butyl glycolate, butyl stearate, triphenyl phosphate, triethyl citrate, camphor, castor oil, esters of citric, stearate, phalic, oleic, phosphate butyric and benzoic acid, glyceryl triacetate and glyceryl triproprionate and mixtures thereof.

Plasticizers included in the compositions of the present invention are in amounts sufficient to provide acceptable flexibility to the nail enamel film on the human or synthetic nail surface. In this regard, the amount of the plasticizers for use in the nail enamel compositions of the present invention range from about 0.5 to 15% by weight, and preferably about 5 to 10% by weight.

The nail enamel compositions of the present invention also contemplate, if desired, the use of phthalate type plasticizers in combination with the preferred plasticizers. For example, it is contemplated the use of plasticizers such as diamylphthalate, dibutyl phthalate, diethyl phthalate, dioctyl phthalate, dibutoxy ethylphthalate and mixtures thereof. These additional plasticizers may be present in the nail enamel composition in the ranges as previously noted.

The nail enamel compositions of the present invention include one or more solvents such as those generally used in conventional nail enamel compositions. Examples of these solvents include ethyl acetate, methyl acetate, ethanol, isopropanol, propyl acetate, n-butanol, xylene, aromatic (containing phenyl groups), amyl acetate, ethers, ketones, alkanes for example, pentane, cyclopentane, hexane, heptane, cyclohexane, cyclic ethers for example, tetrahydrofuran and 1,4-dioxane, cellosolve, butyl cellosolve acetate, cellosolve acetate, methyl cellosolve acetate, butyl cellosolve, ethyl cellosolve, phenylated solvents for example, xylene, esters of acetic acid for example, methyl acetate, ethyl acetate, n-butyl acetate, chlorinated hydrocarbons for example, methylene chloride, chloroform and methylchloroform. It is also contemplated that toluene, if desired, can be included as a solvent or diluent for use in a nail enamel composition in accordance with the compositions of the present invention. The aforementioned solvents can be used alone or in mixtures thereof. In general, the amount of solvent used in the compositions of the present invention range from about 55 to 80% weight, and preferably about 60 to 75% by weight.

In color compositions according to the present invention, one or more pigments and a thixotropic agent are also added. One or more known organic colorants may also be added to these compositions. Pigments are added to the composition to provide cosmetically acceptable shades and to pacify the films. Pigments for use in the present invention may include any of those pigments which are generally known for use in nail enamel compositions. For example, these pigments can include cosmetic grade or purified titanium dioxide, yellow and red iron oxides, bismuth oxychloride, iron blue, iron black, mica particles, ultramarine blue, D&C Red #7, chromide oxide greens, carbon black and lampblack. Other pigments which may be used in compositions according to the present invention may include the Lake pigments, for example, D&C Red #6 barium Lake and D&C Red #7 calcium Lake.

In addition to the above named pigments, there may also be included titanated micas, polyethylene teraphalates and pearl essence which is a suspension of crystalline guanine in nitrocellulose and solvents, as well as other additives which will affect the appearance of the pigment. Although the amount of pigment in the compositions of the present invention will vary as a function of the type of pigment and other components included in the composition, in general, pigments can be included in an amount up to about 15% by weight, and preferably in the amount ranging from about 1 to 4% by weight.

When pigments are included in compositions according to the present invention, it is useful to include a thixotropic agent for enhancing the suspension of the pigments in the other components of the composition. Although a number of thixotropic agents which are generally used in conventional nail enamel compositions may be used to produce compositions according to the present invention, preferred thixotropic agents include the thixotropic clays, especially stearalkonium hectorite, stearalkonium bentonite and mixtures thereof. The thixotropic agent is present in the compositions of the present invention in amounts sufficient to produce a gel, preferably a colloidal gel. In general, the thixotropic agent is included in the amount ranging from about 0.5 to 3% by weight, and preferably in the amount ranging from about 0.7 to 15% by weight.

In addition to the above described components, the compositions of the present invention may also include additional additives including stabilizers, UV light absorbers, fragrances, moisturizers and medicants, depending on the intended result. These components are well known in the art and may be included in amounts well within the teachings of the prior art.

The nail enamel compositions in accordance with the present invention can be manufactured by thoroughly and intimately mixing together all the components in the amounts described in accordance with the present invention. Examples of satisfactory equipment and how to use then are readily apparent to one of ordinary skill in the nail enamel art.

The following examples are provided to illustrate the nail enamel compositions of the present invention and should not be construed to limit the scope of the invention in any way.

|  | WT. % |
|---|---|
| EXAMPLE 1 | |
| nitrocellulose ½ RS | 20.0 (dry) |
| butyl acetate | 35.0 |
| ethyl acetate | 20.0 |
| propyl acetate | 20.0 |
| 2,2,4-trimethyl-1,3-pentanediol diisobutyrate | 5.0 |
|  | 100.00 |
| EXAMPLE 2 | |
| nitrocellulose ½ RS | 20.0 (dry) |
| butyl acetate | 21.0 |
| ethyl acetate | 22.0 |
| propyl acetate | 10.0 |
| isopropyl alcohol | 10.0 |
| 2,2,4-trimethyl-1,3-pentanediol diisobutyrate | 15.0 |
| stearalkonium hectorite | 1.0 |
| D & C Red #6 BA Lake | 0.30 |
| D & C Red #7 CA Lake | 0.10 |

| | WT. % |
|---|---|
| titanium dioxide | 0.50 |
| red iron oxide | 0.10 |
| | 100.00 |

EXAMPLE 3

| | |
|---|---|
| acrylic copolymer Rohm & Haas B-66 | 25.00 |
| polyester resin | 8.00 |
| toluene | 25.00 |
| butyl acetate | 15.00 |
| ethyl acetate | 14.00 |
| isopropyl alcohol | 5.00 |
| 2,2,4-trimethyl-1,3-pentanediol diisobutyrate | 8.00 |
| | 100.00 |

EXAMPLE 4

| | |
|---|---|
| cellulose acetate butyrate CAB 381-0.5 | 25.00 |
| toluenesulfonamide formaldehyde resin | 10.00 |
| toluene | 25.00 |
| butyl acetate | 15.00 |
| ethyl acetate | 14.00 |
| isopropyl alcohol | 5.00 |
| 2,2,4-trimethyl-1,3-pentanediol diisobutyrate | 6.00 |
| | 100.00 |

EXAMPLE 5

| | |
|---|---|
| nitrocellulose ½ RS | 10.05 (dry) |
| nitrocellulose ¼ RS | 4.50 (dry) |
| toluenesulfonamide formaldehyde resin | 8.00 |
| toluene | 25.00 |
| butyl acetate | 25.00 |
| ethyl acetate | 15.00 |
| isopropyl alcohol | 5.00 |
| 2,2,4-trimethyl-1,3-pentanediol diisobutyrate | 4.00 |
| stearalkonium hectorite | 1.00 |
| titanium dioxide | .75 |
| black iron oxide | .10 |
| D & C Red #7 CA Lake | 1.50 |
| phosporic acid 85% | 0.10 |
| | 100.00 |

EXAMPLE 6

| | |
|---|---|
| nitrocellulose ½ sec. | 16.00 (dry) |
| polyester resin | 10.00 |
| butyl acetate | 25.00 |
| ethyl acetate | 22.00 |
| propyl acetate | 10.00 |
| isopropyl alcohol | 10.00 |
| 2,2,4-trimethyl-1,3-pentanediol diisobutyrate | 2.50 |
| dibutyl phthalate | 2.50 |
| stearalkonium hectorite | 1.00 |
| titanium dioxide | .50 |
| red iron oxide | .10 |
| D & C Red #6 Lake | .40 |
| | 100.00 |

EXAMPLE 7

| | |
|---|---|
| nitrocellulose ½ sec. | 12.28 (dry) |
| polyester resin | 8.40 |
| ethyl acetate | 30.75 |
| butyl acetate | 20.70 |
| propyl acetate | 11.00 |
| isopropyl alcohol | 6.17 |
| butyl alcohol | 2.00 |
| 2,2,4-trimethyl-1,3-pentanediol diisobutyrate | 6.50 |
| camphor | 1.00 |
| stearalkonium hectorite | 1.10 |
| benzophenone-1 | .10 |
| | 100.00 |

Although the invention herein has been described with reference to particular embodiments, it is to be understood that the embodiments are merely illustrative of the principles and application of the present invention. It is therefore to be understood that numerous modifications may be made to the embodiments and that other arrangements may be devised without departing from the spirit and scope of the present invention as defined by the claims.

What is claimed is:

1. A human nail enamel composition comprising a film forming polymer, a solvent and a plasticizer comprising at least one or more compounds of the formula:

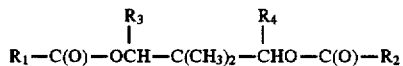

wherein $R_1$ and $R_2$ are the same or different and represent linear or branched alkyl groups containing from one to 18 carbon atoms; and $R_3$ and $R_4$ are the same or different and represent linear or branched alkyl groups containing from one to five carbon atoms, provided that one of $R_3$ or $R_4$ may be hydrogen.

2. The human nail enamel composition of claim 1, wherein $R_1$ and $R_2$ are the same branched chain alkyl groups containing 3 carbon atoms.

3. The human nail enamel composition of claim 1, wherein $R_3$ is a branched chain alkyl group containing 3 carbon atoms and $R_4$ is hydrogen.

4. The human nail enamel composition of claim 1, wherein said plasticizer comprises 2,2,4-trimethyl-1,3-pentanediol diisobutyrate.

5. The human nail enamel composition of claim 1, wherein said plasticizer further includes one or more compounds selected from the group consisting of esters of citric, stearate, phalic, oleic, phosphate, butyric and benzoic acid, camphor, phthalates and mixtures thereof.

6. The human nail enamel composition of claim 1, further including a film forming resin.

7. The human nail enamel composition of claim 6, wherein said film forming resin comprises one or more formaldehyde free resins and mixtures thereof.

8. The human nail enamel composition of claim 6, wherein said film forming resin is selected from the group consisting of polyester resin, epoxy resin and mixtures thereof.

9. The human nail enamel composition of claim 6, further including a thixotropic agent and at least one pigment.

10. The human nail enamel composition of claim 1, wherein said solvent comprises one or more toluene free solvents and mixtures thereof.

11. The human nail enamel composition of claim 1, wherein said plasticizer is present in the range of about 0.5 to 15% by weight.

12. The human nail enamel composition of claim 1, wherein said film forming polymer is present in the range of about 7 to 25% by weight, said solvent is present in the range of about 55 to 80% by weight, and said plasticizer is present in the range of about 0.5 to 15% by weight.

13. A human nail enamel composition comprising about 7 to 25% by weight of nitrocellulose, about 5 to 25% by weight of a film forming resin, about 55 to 80% by weight of at least one solvent, about 0.5 to 15% by weight of 2,2,4-trimethyl-1,3-pentanediol diisobutyrate, and optionally a thixotropic agent and at least one pigment.

14. The human nail enamel composition of claim 13, wherein said nitrocellulose is present in the range of about 10 to 15% by weight, said film forming resin is present in the range of about 8 to 15% by weight, said solvent is present in the range of about 60 to 75% by weight, and said 2,2,4-trimethyl-1,3-pentanediol diisobutyrate is present in the range of about 5 to 10% by weight.

15. The human nail enamel composition of claim 13, wherein said nitrocellulose includes at least one compound selected from the group consisting of nitrocellulose RS 1/8 sec., nitrocellulose RS 1/4 sec., nitrocellulose RS 1/2 sec., nitrocellulose RS 60–80 sec., nitrocellulose RS 5–6 sec. and mixtures thereof.

16. The human nail enamel composition of claim 13, wherein said film forming resin comprises one or more formaldehyde free resins and mixtures thereof.

17. The human nail enamel composition of claim 13, wherein said film forming resin is selected from the group consisting of polyester resin, epoxy resin and mixtures thereof.

18. The human nail enamel composition of claim 17, wherein said epoxy resin comprises tosylamide epoxy resin.

19. The human nail enamel composition of claim 13, wherein said solvent comprises one or more toluene free solvents and mixtures thereof.

20. The human nail enamel composition of claim 13, wherein said nitrocellulose is present in an amount greater than the amount of said film forming resin.

21. A human toluene formaldehyde free nail enamel composition comprising a film forming polymer, a formaldehyde free film forming resin, one or more toluene free solvents and mixtures thereof, a plasticizer comprising at least one or more compounds of the formula:

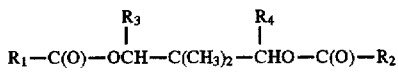

wherein $R_1$ and $R_2$ are the same or different and represent linear or branched alkyl groups containing from one to 18 carbon atoms; and $R_3$ and $R_4$ are the same or different and represent linear or branched alkyl groups containing from one to five carbon atoms, provided that one of $R_3$ or $R_4$ may be hydrogen, and optionally a thixotropic agent and at least one pigment.

22. The human nail enamel composition of claim 21, wherein said film forming polymer comprises nitrocellulose.

23. The human nail enamel composition of claim 22, wherein said nitrocellulose includes at least one compound selected from the group consisting of nitrocellulose RS 1/8 sec., nitrocellulose RS 1/4 sec., nitrocellulose RS 1/2 sec., nitrocellulose RS 60–80 sec., nitrocellulose RS 5–6 sec. and mixtures thereof.

24. The human nail enamel composition of claim 21, wherein said nitrocellulose is present in the range of about 7 to 25% by weight, said film forming resin is present in the range of about 5 to 25% by weight, said solvent is present in the range of about 55 to 80% by weight, and said 2,2,4-trimethyl-1,3-pentanediol diisobutyrate is present in the range of about 0.5 to 15% by weight.

25. The human nail enamel composition of claim 21, wherein said plasticizer comprises 2,2,4-trimethyl-1,3-pentanediol diisobutyrate.

26. The human nail enamel composition of claim 21, wherein said film forming resin is selected from the group consisting of polyester resin, epoxy resin and mixtures thereof.

27. The human nail enamel composition of claim 26, wherein said epoxy resin comprises tosylamide epoxy resin.

28. The human nail enamel composition of claim 21, wherein said film forming polymer is present in an amount greater than the amount of said film forming resin.

29. The human nail enamel composition of claim 21, wherein said solvents are selected from the group consisting of ethyl acetate, butyl acetate, isopropyl alcohol and mixtures thereof.

30. The human nail enamel composition of claim 29, wherein said film forming resin comprises a mixture of polyester resin and tosylamide epoxy resin.

31. The human nail enamel composition of claim 21, wherein said plasticizer further includes esters of citric, stearate, phalic, oleic, phosphate, butyric and benzoic acid, camphor, phthalates and mixtures thereof.

32. A human toluene formaldehyde free nail enamel composition consisting essentially of about 7 to 25% by weight of nitrocellulose, about 5 to 25% by weight of one or more formaldehyde free film forming resins and mixtures thereof, about 55 to 80% by weight of one or more toluene free solvents and mixtures thereof, about 0.5 to 15% by weight of a plasticizer consisting essentially of at least one or more compounds of the formula:

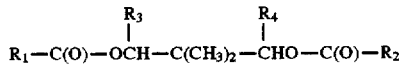

wherein $R_1$ and $R_2$ are the same or different and represent linear or branched alkyl groups containing from one to 18 carbon atoms; and $R_3$ and $R_4$ are the same or different and represent linear or branched alkyl groups containing from one to five carbon atoms, provided that one of $R_3$ or $R_4$ may be hydrogen, and optionally a thixotropic agent and at least one pigment.

33. The human nail enamel composition of claim 32, wherein said plasticizer comprises 2,2,4-trimethyl-1,3-pentanediol diisobutyrate.

34. The human nail enamel composition of claim 32, wherein said nitrocellulose is present in the range of about 10 to 15% by weight, said film forming resin is present in the range of about 8 to 15% by weight, said solvent is present in the range of about 60 to 75% by weight, and said 2,2,4-trimethyl-1,3-pentanediol diisobutyrate is present in the range of about 5 to 10% by weight.

35. The human nail enamel composition of claim 32, wherein said film forming resin is selected from the group consisting of polyester resin, epoxy resin and mixtures thereof.

36. The human nail enamel composition of claim 35, wherein said epoxy resin comprises tosylamide epoxy resin.

37. The human nail enamel composition of claim 32, wherein said film forming polymer is present in an amount greater than the amount of said film forming resin.

38. The human nail enamel composition of claim 32, wherein said solvents are selected from the group consisting of ethyl acetate, butyl acetate, isopropyl alcohol and mixtures thereof.

* * * * *